United States Patent [19]

Danulat et al.

[11] 4,278,505

[45] Jul. 14, 1981

[54] PROCESS OF RECOVERING AN N-HEXANE PRODUCT WHICH IS FREE FROM AROMATIC COMPOUNDS

[75] Inventors: Hans F. Danulat, Frankfurt am Main; Kamar P. John, Bad Homburg; Helmut Klein, Hanau; Stephen Lukatsch, Dietzenbach, all of Fed. Rep. of Germany

[73] Assignee: Metallgesellschaft Aktiengesellschaft, Frankfurt am Main, Fed. Rep. of Germany

[21] Appl. No.: 949,467

[22] Filed: Oct. 10, 1978

[30] Foreign Application Priority Data

Oct. 11, 1977 [DE] Fed. Rep. of Germany ....... 2745672

[51] Int. Cl.$^3$ ............................................. B01D 3/40
[52] U.S. Cl. ....................................... 203/59; 203/58; 203/62; 203/75; 203/77; 203/78; 203/82; 203/84; 203/93; 203/94; 208/313; 585/862; 585/863
[58] Field of Search .............. 585/833, 860, 862, 863; 208/313; 203/43, 44, 58, 59, 62, 71, 73, 74, 77, 80, 81, 91, 99, DIG. 19, 75, 78, 82, 84, 93, 94

[56] References Cited

U.S. PATENT DOCUMENTS

| | | | |
|---|---|---|---|
| 2,325,319 | 7/1943 | Durrum | 208/313 |
| 2,361,493 | 10/1944 | Patterson | 203/81 |
| 2,842,484 | 7/1958 | Fleck | 203/59 |
| 2,848,387 | 8/1958 | Glazier et al. | 203/71 |
| 3,317,627 | 5/1967 | King et al. | 585/860 |
| 3,415,739 | 12/1968 | Eisenlohr et al. | 585/862 |
| 3,707,575 | 12/1972 | Muller et al. | 203/59 |
| 3,725,255 | 4/1973 | Barilli et al. | 203/59 |

Primary Examiner—Frank Sever
Attorney, Agent, or Firm—Sprung, Felfe, Horn, Lynch & Kramer

[57] ABSTRACT

A process of recovering an n-hexane product which is free from aromatic compounds by extractive distillation from a mixture of aromatic and non-aromatic compounds. The mixture is fed to and distilled in a first distillation column, from which a benzene-containing sump product and the overhead product consisting of non-aromatic compounds are withdrawn. The distillate is laterally withdrawn above the feeding point of the feed mixture and transferred to the upper portion of a second distillation column. The hexane cut is withdrawn as sump product from the second distillation column and fed to an extractive distillation column approximately in the middle thereof and is extracted in the extractive distillation column with a selective solvent which is fed above the feeding point of the hexane cut consisting of the sump product of the second distillation column. The sump product containing the selective solvent is withdrawn from the extractive distillation column and the overhead thereof vapors are condensed. The condensate is withdrawn as an n-hexane product that is free from aromatic compounds.

9 Claims, 1 Drawing Figure

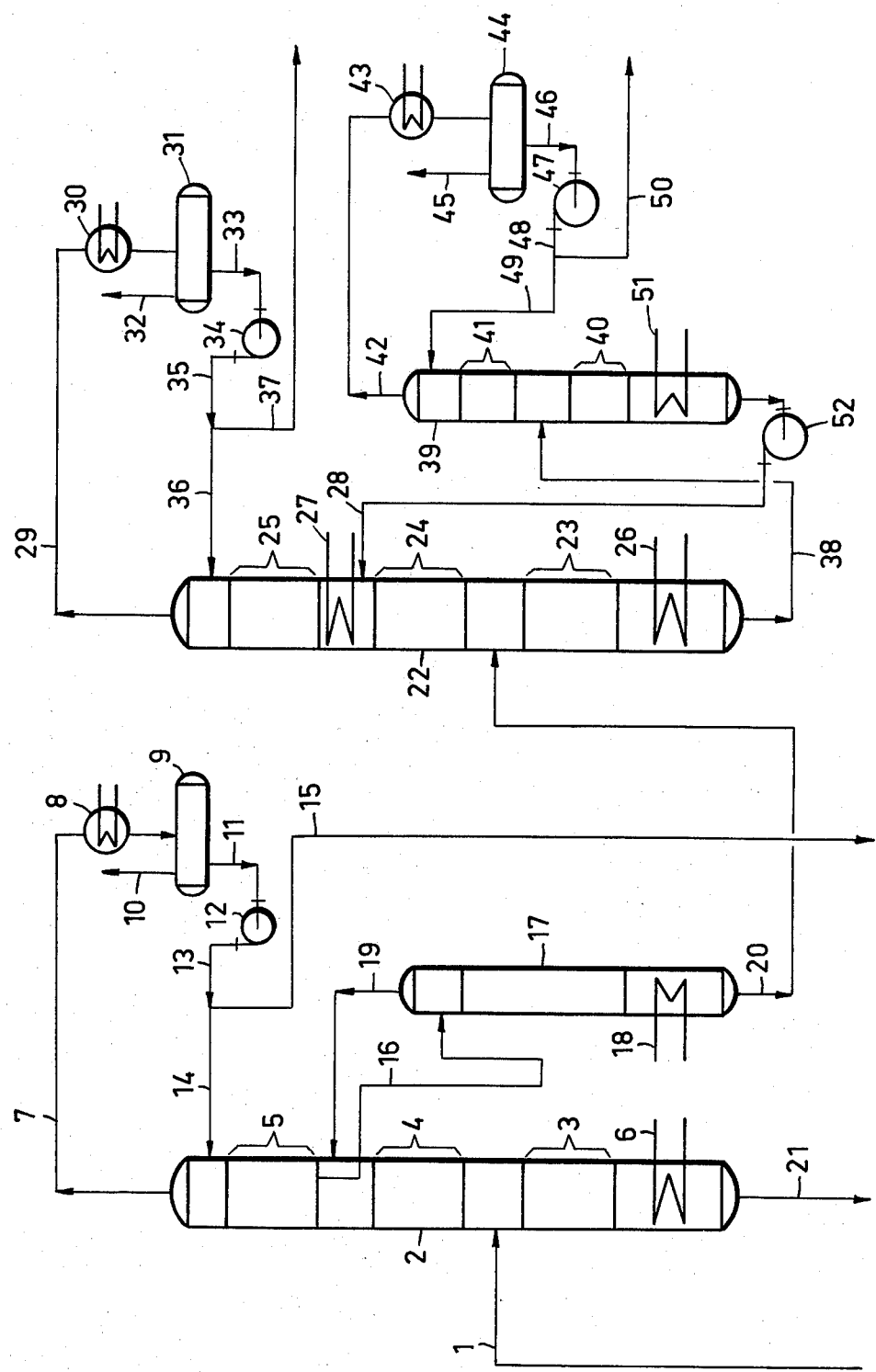

PROCESS OF RECOVERING AN N-HEXANE PRODUCT WHICH IS FREE FROM AROMATIC COMPOUNDS

This invention relates to a process of recovering an n-hexane product which is free from aromatic compounds by extractive distillation from a mixture of aromatic and non-aromatic compounds.

Hexane is used in industry as a solvent, also as an extracting solvent, e.g., for extracting oil seeds, and is constantly gaining in importance. For numerous uses e.g., in the foodstuffs-processing industry, an n-hexane product which is free from aromatic compounds is required.

It is known to separate aromatic compounds from mixtures with non-aromatic compounds by a liquid-liquid extraction or extractive distillation or said mixtures. These separating methods may also be combined.

For instance, in a known process of recovering pure aromatic compounds from hydrocarbon mixtures which contain aromatic compounds, the mixture is subjected to extraction and extractive distillation with a polar solvent and the extract which contains aromatic compounds and is free from non-aromatic compounds is subjected to distillation. In that process, the entire mixture to be processed is subjected to extractive distillation and the resulting sump product which is free of non-aromatics is subjected in known manner to distillation so that pure aromatic compounds are recovered therefrom. The overhead product obtained by the distillation contains all non-aromatic compounds as well as 5 to 30%, preferably 10 to 20%, of the aromatic compounds of the feed mixture, and in a succeeding multistage liquid-liquid extraction is divided into a non-aromatic raffinate and an extract, which contains the aromatic content of the overhead product and is recycled to the upper part portion of the extractive distillation column (German patent specification No. 14,68,315).

It is also known to recover pure aromatic hydrocarbons from mixtures thereof with non-aromatic hydrocarbons by solvent extraction and/or extractive distillation with the aid of a selective solvent, which has a distinctly higher boiling point than the aromatic compounds to be recovered, to subject the raw feed mixture to a preliminary distillation so as to obtain a mixture which is enriched in aromatic content and is then subjected to the solvent extraction or extractive distillation, to reflux part of the distillate to the preliminary distillation step, and to replace part of said recycled distillate by an anhydrous selective solvent which has a distinctly higher boiling point than the aromatic compounds to be recovered (Opened German specification No. 21,22,770).

In another process of recovering pure aromatic compounds from mixtures thereof with non-aromatic compounds boiling in the same range as the aromatic compounds, which mixtures have an aromatic content below 60% by weight, the mixture is subjected to extractive distillation with a selective solvent, which serves to separate aromatic from non-aromatic compounds. Part of said solvent is fed to one of the upper plates of a first column, which precedes the extractive distillation column proper, an overhead product is withdrawn from said first column, a mixture which comprises non-aromatic compounds, solvent and aromatic compounds and has a high content of the latter is withdrawn from the sump of the first column, and said sump product is processed in known manner by extractive distillation to recover pure aromatic compounds (Opened German specification No. 24 24 349).

In another known process of separating n-hexane from its mixtures with benzene, the recovery of an n-hexane product of high purity is ensured in that the separation is effected in a single rectifying step under a pressure between 3 and 10 bars in a column having a capacity of about 40 theoretical plates, i.e., under operating conditions resulting in a separation of the azeotropic mixture which consists of n-hexane and benzene (East German patent specification No. 31,301).

In these and similar processes, the yield of aromatic compounds are recovered depends on the operating conditions of the plant. In the processing of coke oven benzene, the yield of pure benzene usually amounts to 98 to 99% of the benzene contained in the feedstock. Where benzene cuts are processed which have been recovered from thermally cracked gasoline or reformate, the refined product contains about 3 to 10% pure benzene. A higher loss of pure benzene in the refined product would mean lower operating costs of the plant but would decrease the yield of pure benzene to such an extent that the recovery of benzene would no longer be economical. A higher yield is in most cases not optimal regarding the energy requirement and will result in a less economical operation.

It is an object of the invention to avoid these and other disadvantages of the state of the art and to provide a simple and economical process of recovering an n-hexane product which is free from aromatic compounds. More specifically, the new process should be distinguished by a low energy requirement and should simplify the recovery of n-hexane, which owing to the coexistance of isoparaffin and cyclic hydrocarbon with the benzene was highly expensive so far and required a fine distillation.

This object is accomplished according to the invention in that a feed mixture of aromatic and non-aromatic compounds is distilled in a two-column system to recover a hexane cut consisting of hexane, benzene, and small quantities of non-aromatic compounds which boil in the same range as hexane and benzene, which distillation is effected in that the mixture of aromatic and non-aromatic compounds is fed to a first distillation column and distilled therein, a benzene-containing sump product and an overhead product consisting of the low-boiling non-aromatic compounds are withdrawn from the first distillation column and a distillate is laterally withdrawn from the first distillation column at a point disposed above the feeding point of the feed mixture of aromatic and non-aromatic compounds and is transferred to the upper portion of a second distillation column, a sump product consisting of the hexane cut is withdrawn from the second distillation column and is fed to an extractive distillation column approximately in the middle thereof and extracted therein with a selective solvent, which is fed to the extractive distillation column above the feeding point of the hexane cut consisting of the sump product of the second distillation column, a sump product containing the selective solvent is withdrawn from the extractive distillation column, vapors are withdrawn overhead from the extractive distillation column and condensed, and the condensate is withdrawn as an n-hexane product which is free from aromatic compounds.

According to a preferred further feature of the invention, the feed mixture of aromatic and non-aromatic compounds is fed to the first distillation column approximately in the middle thereof.

According to a preferred further feature of the invention the overhead product of the first distillation column is condensed and is partly refluxed to the top of the first distillation column.

In a preferred embodiment, part of the condensed overhead product of the extractive distillation column, consisting of an n-hexane product which is free from aromatic compounds is recycled to the upper portion of the extractive distillation column.

Within the scope of the invention, the sump product of the extractive distillation column, which contains benzene and selective solvent, may be transferred to a stripping column and stripped therein, whereafter the overhead vapors of the stripping column are condensed, and the condensate is withdrawn and partly recycled to the upper portion of the stripping column.

The selective solvent which becomes available in the stripping column as a sump product is preferably recycled to the extractive distillation column.

N-Methylpyrrolidone is preferably used as a selective solvent within the scope of the invention.

According to a preferred further feature of the invention the benzene-containing condensate formed from the overhead vapors of the stripping column and the benzene-containing sump product of the first distillation column are separately or jointly processed for the recovery of benzene.

Within the scope of the invention, an existing extractive distillation column for recovering the feed mixture of aromatic and non-aromatic compounds may be used rather than the stripping column.

The advantages afforded by the invention reside particularly in that a simple and economic process is provided by which an n-hexane product which is free from aromatic compounds, can be recovered by extractive distillation from any desired mixtures with aromatic and non-aromatic compounds. The novel process has a very low energy requirement.

Besides, the process enables an ecologically satisfactory recovery of all components of the feed mixture. Specifically, benzene of high purity can be recovered in a high yield.

Because hexane is recovered at a low temperature within the scope of the invention, the entire distillation system can be heated mainly with hot solvent and only a small quantity of low-pressure steam or condensate is required. About 1.7 tons of steam at 3 bars and about 17.9 tons of condensate are required per ton of hexane and the condensate is cooled from 133° to 100° C. in the process.

With reference to the drawing and an Example, the invention will now be described and explained in more detail.

EXAMPLE

The overhead product (raffinate) of an extractive distillation plant (not shown) is fed in conduit 1 to a preliminary distillation column 2. That overhead product has the following composition:

| | Rate kg/h | Boiling point at 1 kg/sq.cm. absolute pressure °C. |
|---|---|---|
| Cyclopentane | 585 | 49.3 |
| 3-Methylpentane | 534 | 63.3 |
| n-Hexane | 1145 | 68.7 |
| Methylpentane | 3777 | 71.8 |
| Benzene | 1086 | 80.178 |
| Cyclohexane | 1403 | 80.7 |
| Isoheptane | 1613 | 90.0 |
| Dimethylcyclopentane | 1208 | 90.8 |
| n-Heptane | 1027 | 98.4 |
| Methycyclohexane | 149 | 100.9 |
| | 12527 kg/h | |

The sump product of the preliminary distillation column 2 is withdrawn through conduit 21 and has the following composition:

| | Rate kg/h |
|---|---|
| 3-Methylpentane | 2 |
| n-Hexane | 95 |
| Methylpentane | 1300 |
| Benzene | 350 |
| Cyclohexane | 1053 |
| Isoheptane | 1605 |
| Dimethylcyclopentane | 1208 |
| n-Heptane | 1027 |
| Methylcyclohexane | 149 |
| | 6789 kg/h. |

The column is supplied with heat for distillation through a heating register 6. The column contains plates which are suitably combined in sets 3, 4, and 5. The raffinate is fed through conduit 1 between sets 3 and 4. Overhead vapors are withdrawn through conduit 7 and condensed in condenser 8. The condensate is collected in a reflux vessel 9. The column is pressurized via conduit 10. The liquefied overhead product is pumped by pump 12 in conduit 13 and part of it is refluxed through column 14. Low-boiling non-aromatic compounds are delivered as a final product through conduit 15. They have the following composition:

| | Rate kg/h |
|---|---|
| Cyclopentane | 556 |
| 3-Methylpentane | 282 |
| n-Hexane | 40 |
| | 878 kg/h. |

A liquid product is laterally withdrawn through conduit 16 from the lower portion of the plate set 5 and is transferred to a second column 17. The latter contains only a single set of plates, consisting of about 40 exchange plates. Heat for distillation is supplied to column 17 through a heating register 18. The overhead vapors from column 17 are recycled through conduit 19 to column 2. The sump product of column 17 is fed via conduit 20 to an extractive distillation column 22. The product flowing in conduit 20 is the hexane fraction, which has the following composition:

| | Rate kg/h |
|---|---|
| Cyclopentane | 29 |
| 3-Methylpentane | 250 |
| n-Hexane | 1010 |
| Methylpentane | 2477 |
| Benzene | 736 |
| Cyclohexane | 350 |
| Isoheptane | 8 |
| | 4860 kg/h. |

The extractive distillation column 22 comprises a heating system 26, sets of plates 23, 24, 25 and a reboiler 27. N-methylpyrrolidone as solvent is fed through conduit 28 to the plates of set 24 at a rate of 20,000 kg/h. The sump product has the following composition:

| | Rate kg/h |
|---|---|
| Cyclopentane | 4 |
| 3-Methylpentane | 40 |
| n-Hexane | 5 |
| Methylpentane | 2377 |
| Benzene | 736 |
| Cyclohexane | 350 |
| Isoheptane | 8 |
| N-methylpyrrolidone | 20000 |
| | 23520 kg/h. |

The sump product is withdrawn through conduit 38 and is fed either to the preceding extractive distillation column (not shown) or to a succeeding stripping column 39. The overhead vapor from column 22 is fed through conduit 29 to a condenser 30 and is liquefied therein. The condensate flows into a reflux vessel 31. The column is pressurized by conduit 32. The liquefied overhead product is withdrawn through conduits 33 and pumped by pump 34 through conduit 35 and is partly refluxed through conduit 36 and partly withdrawn through conduit 37 as an end product which consists mainly of n-hexane and is free from aromatic compounds and has the following composition:

| | Rate kg/h |
|---|---|
| Cyclopentane | 25 |
| 3-Methylpentane | 210 |
| n-Hexane | 1005 |
| Methylpentane | 100 |
| | 1340 kg/h. |

From the hexane cut which is fed through conduit 20 to the extractive distillation column 22, benzene and the undesired non-aromatic compounds are removed in the plate sets 24 and 23 below the feeding point of the N-Methylpyrrolidone. With the aid of the heating register 27 and under the influence of the reflux through conduit 36, the hexane is purified in the plate set 25 to remove traces of upwardly entrained N-methylpyrrolidone.

From a stripping column 39, which comprises a heating register 51 and sets 40 and 41 of plates, a sump product consisting of the N-methylpyrrolidone is withdrawn through conduit 28 by a pump 52 and is fed to the extractive distillation column 22. The overhead vapors are withdrawn from the stripping column 39 through conduit 42 and are liquefied in a condenser 43. The condensate is collected in a reflux vessel 44. The stripping column 39 is pressurized through conduit 45. By means of the pump 47, the overhead product is withdrawn through conduit 46 and pumped through conduit 48 and partly refluxed through conduit 49 to column 39 and partly withdrawn as a product via conduit 50. That product has the following composition:

| | Rate kg/h |
|---|---|
| Cyclopentane | 4 |
| 3-Methylpentane | 40 |
| n-Hexane | 5 |
| Methylpentane | 2377 |
| Benzene | 736 |
| Cyclohexane | 350 |
| Isoheptane | 8 |
| | 3520 kg/h. |

In this case the non-aromatic compounds withdrawn through conduit 21 still contain benzene. The non-aromatic compounds withdrawn through conduit 15 are free from benzene. The n-hexane product withdrawn through conduit 37 is free from aromatic compounds and from solvent. The benzene withdrawn through conduit 50 still contains non-aromatic compounds and is free from solvents.

If the extractive distillation plant for recovering benzene which precedes the present system and serves to recover benzene is used rather than the column 39, conduit 38 is connected to the feed pipe leading to the extractive distillation column of that extractive distillation plant. In that case the solvent is fed through conduit 28 to the extractive distillation column 22 and is taken as a partial stream from the sump of the existing stripping column. The additional quantity of benzene recovered in the raffinate by extractive distillation (that refined product is fed in conduit 1) becomes available at the top of the stripping column so that the benzene yield there amounts to about 100%.

The preliminary distillation column system comprising the columns 2 and 17 operate under a head pressure of 1.3 bars. This results in sump temperatures of 80° to 90° C. The extractive distillation column 22 operates under a head pressure of 0.8 bars and has a sump temperature of about 108° C. The stripping column operates at a sump temperature of 165° C. and a pressure of 0.5 bars. The possibilities of exchanging heat are not shown on the drawing. From the foregoing it is apparent that almost the entire heat content delivered by the solvent as a result of a temperature drop from 165° to 60° C. can be used to heat the distillation columns. A supply of extraneous heat is required only for the heating register of the extractive distillation column 26. Steam at 3 bars is used for heating, in the present case at a rate of 1700 kg/h. Condensate from that steam and extraneous condensate are used to heat column 2 and are required at a rate of 19600 kg/h. When an extractive distillation plant is available for a recovery of benzene, that plant delivers heat at a rate of 1,500,000 kcal/h for heating the present plant. When a separate stripping column is required, that heat quantity must be supplied as steam at 10 to 12 bars. The values stated in the Example are applicable for an n-hexane yield of 90% if the quantity of n-hexane fed in conduit 1 is taken as 100%.

| If | |
|---|---|
| one ton of steam is valued at | DM 25,— |
| one ton of raffinate at | DM 390,— |
| one ton of n-hexane product at | DM 690,— |
| one ton of benzene at | DM 750,— | the following prices will be obtained for the products recovered in the foregoing Example:

| | |
|---|---|
| n-Hexane product | DM 910,—/h |
| Benzene | DM 530,—/h |
| Refined product | DM 4100,—/h |
| | DM 5540,—/h. |
| The raffinate costs | DM 4900,—/h |
| Steam | DM 43,—/h |
| Extraneous condensate | DM 40,—/h |
| Total | DM 4983,—/h |
| The profit amounts to DM 557,—/h. | |

This profit will be obtained if the hexane-recovering and de-aromating plant succeeds an existing extractive distillation plant. If a separate stripping column must be operated, additional steam at 2.3 tons per hour will be required so that the costs rise by DM 57,-/h and the profit is decreased by DM 57,-/h to DM 500,-/h.

The first distillation column 2 can have between 30 and 40 theoretical plates, preferably between 32 and 38 theoretical plates. The n-hexane-aromatic feed from line 1 can enter between the tenth and eleventh plates. Generally, it is inserted at a point from the bottom between 25% to 30% the distance from the sump to the top of the column. The column 2 is maintained at a temperature between 80° and 90° C. at the sump and 60° and 70° C. at the top. The column can be operated at a pressure of 1,000 to 1,200 mm Hg, preferably atmospheric pressure.

The n-hexane containing fraction is withdrawn in line 16 at a point from the bottom between 68% to 73% the distance from the sump to the top of the column such as at a point between the twenty-third and twenty-fourth theoretical plates (counting from the bottom). It is inserted into column 17 at a point from 100% of the distance from the sump of column 17 to the top of column 17. Column 17 can have 18 to 25 theoretical plates and the n-hexane side cut from column 2 can be introduced in column 17 on the eighteenth or twenty-fifth theoretical plates (counting from the bottom). Column 17 is operated at a pressure of 1,100 to 1,200 mm Hg, preferably at atmospheric pressure. The sump temperature is 78° to 85° C., preferably 79° to 83° C., while a temperature of 68° to 72° C., preferably 69° to 71° C., is maintained at the top of the column 17.

The n-hexane containing sump product is introduced into the extraction distillation column 22 at a point from the bottom between 35% and 42% of the distance between the sump and the top of the column, while the solvent is introduced thereabove at a point from the bottom between 78% and 82% of the distance between the sump and the top of the column. The solvent is employed in an amount of 3 to 4.5 volumes per volume of n-hexane containing mixture entering via line 20. The temperature at the sump of the extractive distillation column 22 is between 100° and 115° C., while the temperature at the top of column 22 is 61° to 68° C. The pressure in column 22 can be 600 to 760 mm Hg. Suitable solvents for use in the extractive distillation include NMP.

The stripping column 39 has 24 theoretical plates, feed is introduced at 16% from the sump. Operating pressure at the top is 380 mm HG. Sump temperature is 165° C. and the top temperature is 60° C.

What is claimed is:

1. A process of recovering an n-hexane product which is substantially free from aromatic compounds by extractably distilling the same from a mixture of aromatic and non-aromatic compounds, consisting essentially of distilling a feed mixture of aromatic and non-aromatic compounds in a two column system to recover a hexane cut consisting of hexane, benzene and small quantities of non-aromatic compounds which boil in the same range as hexane and benzene, which distillation is effected by feeding the mixture of non-aromatic compounds to a first distillation column approximately in the middle thereof and distilling the same therein, withdrawing a benzene-containing sump product and an overhead product consisting of low-boiling non-aromatic compounds from the first distillation, and withdrawing a distillate laterally from the first distillation, at a point disposed above the feeding point of the feed mixture of aromatic and non-aromatic compounds and transferring the same to the upper portion of a second distillation column, withdrawing a sump product consisting of hexane, benzene and small amounts of non-aromatics boiling in the range of both of said components from the second distillation column and feeding the same to an extractive distillation column approximately in the middle thereof and extracting the same therein with an extractive solvent by feeding into the extractive distillation column above the feeding point of the hexane cut consisting of the sump product of the second distillation column, withdrawing a sump product containing the selective solvent from the extractive distillation column, withdrawing vapors overhead from the extractive distillation column and condensing the same and withdrawing the condensate as an N-hexane product of a purity sufficient for use in food processing.

2. A process according to claim 1, by feeding the feed mixture of aromatic and non-aromatic compounds to the first distillation column approximately in the middle thereof.

3. A process according to claim 1 characterized by condensing the overhead product of the first distillation column and partly refluxing the same to the top of the first distillation column.

4. A process according to claim 1 further comprising recycling part of the condensed overhead product of the extractive distillation, consisting of an n-hexane product which is free from aromatic compounds to the upper portion of the extractive distillation column.

5. A process according to claim 1 further comprising transferring the sump product of the extractive distillation column, which sump product contains benzene and a selective solvent, to a stripping column and stripping the same therein, condensing the overhead vapors of the stripping column and withdrawing the condensate and partly recycling the same to the upper portion of the stripping column.

6. A process according to claim 5 further comprising separately or jointly processing the benzene-containing condensate formed from the overhead vapors of the stripping column and the benzene-containing sump product of the first distillation column for the recovery of benzene.

7. A process according to claim 1 further comprising recycling the selective solvent which becomes available in the stripping column as a sump product to the extractive distillation column.

8. A process according to any of the preceding claims 1 to 6, wherein N-methylpyrrolidone is the selective solvent.

9. A process according to claim 1 further comprising transferring sump product of the extractive distillation column, which sump product contains benzene and a selective solvent, to an existing extractive distillation column employed for recovering the feed mixture of aromatic and non-aromatic compounds.

* * * * *